United States Patent [19]
Tohda et al.

[11] Patent Number: 5,817,478
[45] Date of Patent: Oct. 6, 1998

[54] MULTICLONING VECTOR, EXPRESSION VECTOR AND PRODUCTION OF FOREIGN PROTEINS BY USING THE EXPRESSION VECTOR

[75] Inventors: Hideki Tohda; Yuko Hama; Hiromichi Kumagai, all of Yokohama, Japan

[73] Assignee: Asahi Glass Company Ltd., Tokyo, Japan

[21] Appl. No.: 446,729

[22] PCT Filed: Oct. 4, 1994

[86] PCT No.: PCT/JP94/01657

§ 371 Date: Jul. 24, 1995

§ 102(e) Date: Jul. 24, 1995

[87] PCT Pub. No.: WO95/09914

PCT Pub. Date: Apr. 13, 1995

[30] Foreign Application Priority Data

Oct. 5, 1993 [JP] Japan ................................. 5-249810

[51] Int. Cl.⁶ ..................... C12P 21/02; C12N 15/64; C12N 15/81; C07H 21/04
[52] U.S. Cl. ................ 435/69.1; 435/172.1; 435/255.1; 435/320.1; 536/23.1; 536/24.1; 536/24.2
[58] Field of Search ..................... 435/69.1, 70.1, 435/71.1, 172.1, 320.1, 255.1; 536/24.1, 24.2, 23.1; 935/22, 23, 33, 34, 37, 66, 69

[56] References Cited

FOREIGN PATENT DOCUMENTS

| 0121569 | 10/1984 | European Pat. Off. . |
| 0214638 | 3/1987 | European Pat. Off. . |
| 2598430 | 11/1987 | France . |
| 5 15380 | 1/1993 | Japan . |

OTHER PUBLICATIONS

Whitehead et al. "Three Restriction Endonucleases from Anabaena–flos–Aquae" J Gen Microbiol 131 951–858 1985.

*Primary Examiner*—Nancy Degen
*Attorney, Agent, or Firm*—Oblon, Spivak, McClelland, Maier & Neustadt, P.C.

[57] ABSTRACT

The present invention relates to an expression vector capable of being expressed in a fission yeast *Schizosaccharomyces pombe*, a multicloning vector for construction of the expression vector, a method of constructing the expression vector, a transformant carrying the expression vector, and a method of producing a foreign protein using the transformant. The multicloning vector has a sequence of -ACATGT-from the 5' direction, as a restriction enzyme recognition site for introduction of a structural gene of a foreign protein at the front end of its multicloning site. To construct the expression vector, the structural gene of the foreign protein is introduced by using the restriction enzyme recognition site so that the front end of the introduced structural gene of the foreign protein has a sequence of -ACATGN- (wherein N is an arbitrary base) from the 5' direction, and ATG in the sequence functions as the translation initiation site for the structural gene of the foreign protein. Since the base N next to ATG in the sequence in the expression vector may be any base, it is possible to introduce a structural gene of any foreign protein to the vector. In addition, the present invention can increase the expression amount of the foreign protein.

12 Claims, 12 Drawing Sheets

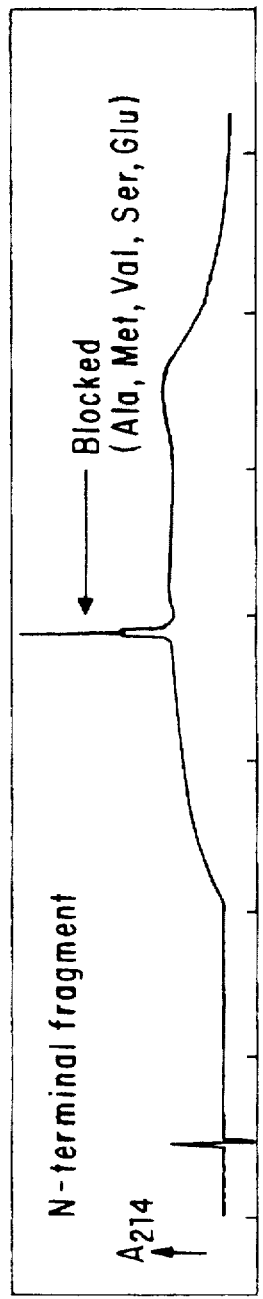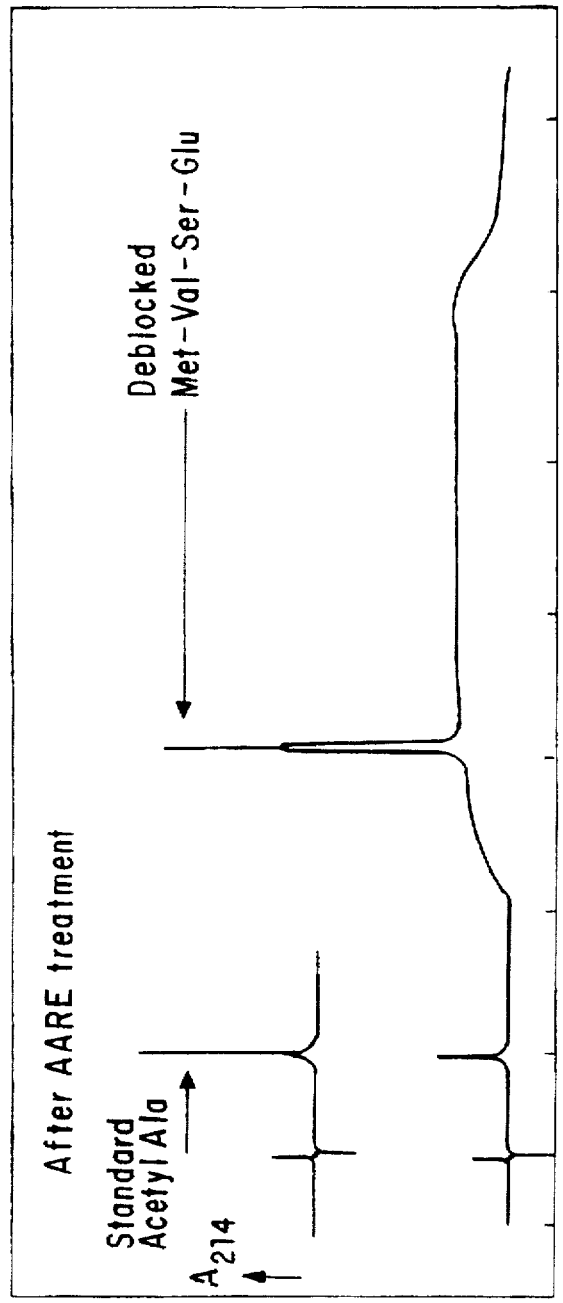
FIG. 10A
FIG. 10B

MULTICLONING VECTOR, EXPRESSION VECTOR AND PRODUCTION OF FOREIGN PROTEINS BY USING THE EXPRESSION VECTOR

TECHNICAL FIELD

The present invention relates to a multicloning vector which enables a fission yeast *Schizosaccharomyces pombe* (hereinafter referred to as *S.pombe*) to produce a foreign protein, an expression vector which is obtainable by introducing a gene of a foreign protein into the multicloning vector, a method of preparing the expression vector, a *S.Pombe* transformant which carries the expression vector, and a method of producing a foreign protein by using the transformant. The present invention enables genes of various foreign proteins to be expressed efficiently and thereby reduces the cost for production of the resulting peptides or proteins.

BACKGROUND ART

Production of foreign proteins utilizing genetic recombination technology has been extensively conducted by using microorganisms such as *Escherichia coli*, *Saccharomyces cerevisiae* or Bacillus, animal cells (inclusive of insect cells) and plant cells. As such foreign proteins, various biogenic polypeptides are considered to be accessible, and many of them have been industrially produced for medical use so far.

However, methods employing procaryotes are not effective for all polypeptides, and it is not always easy to reproduce the complicated post-translational modification of eucaryotic proteins and to reproduce the natural steric structures. Actually, some products by procaryotic cells are known to be kept away from application to medicines and the like, due to their irregular structures and activities (Proc. Natl. Acad. Sci. USA, 86, 3428–3432, 1989). In addition, *Escherichia coli* has a characteristic endotoxin, which might contaminate end products.

In methods employing animal or plant cells, production efficiency is low, because these cells are more difficult to handle than microorganisms, their culture is costly, and they are obtainable only at low cell densities. For this reason, the most ideal organisms for production of foreign proteins, especially eucaryotic polypeptides, to be yeasts, eucaryotic microorganism. Yeasts are advantageous in view of their established culture methods and their ability to express genetic information of eucaryotes. Further, these have been conventionally used in fermentation and food industries, are sure to be safe to human bodies, and have a characteristic that they do not contain endotoxins. Among yeasts, *S.pombe* is considered to be closer to animal cells in properties than *Saccharomyces cerevisiae*. Therefore, use of *S.pombe* has a host for expression of a foreign protein is expected to provide a gene product closer to its natural form, like that produced by animal cells. Since yeasts have a lot of commonness in their culture methods, knowledges about other yeasts can be easily applied to the yeast. Therefore, it is obviously advantageous to use *S.pombe* for production of a foreign protein by using microbiological methods and the DNA recombination technique.

However, *S.pombe* is far behind *Escherichia coli* and *Saccharomyces cerevisiae* in studies on genetic recombination using them. Especially, with respect to gene expression in *S.pombe*, only a small number of studies have been reported, such as Japanese Unexamined Patent Publications Nos. 181397/1986, 283288/1990 and 63596/1992. This is because there is no expression vector which has a powerful promoter and can be present stably in *S.pombe* cells and to which a gene is most suitably and easily introduced.

The present inventors proposed an expression vector capable of resolving the above-mentioned problems (Japanese Unexamined Patent Publication No.15380/1993). However, the expression vector is still insufficient to adequately express genes of foreign proteins, and further improved expression vectors are demanded.

DISCLOSURE OF INVENTION

The present inventors have studies from the above-mentioned aspects, and, as a result, constructed an expression vector that enables the gene of a desired foreign protein to be expressed adequately, by modifying the translation initiation site of the gene of the foreign protein into a restriction enzyme recognition site. The present invention relates to a multicloning vector which enables *S.pombe* to produce a foreign protein, an expression vector constructed by introducing the structural gene of a foreign protein into the multicloning vector, a method of constructing the expression vector, a *S.pombe* transformant carrying the expression vector and a method of producing a foreign protein by using the transformant, and provides:

(1) a multicloning vector which has a promoter region capable of functioning in an eucaryotic cell and a multicloning site for introduction of a structural gene of a foreign protein to be governed by the promoter downstream from the promoter region, wherein a restriction enzyme recognition site at the front end of the multicloning site of the vector for introduction of the structural gene of the foreign protein has a sequence of -ACATGT- from the 5' direction;

(2) an expression vector which has a promoter region capable of functioning in an eucaryotic cell and a structural gene of a foreign protein governed by the promoter downstream from the promoter region, wherein the structural gene of the foreign protein has a sequence of -ACATGN- (wherein N is an arbitrary base) from the 5' direction at its front end, ATG in the sequence is the translation initiation site of the structural gene of the foreign protein, and the sequence is derived from the recognition enzyme recognition site for introduction of the structural gene of the foreign protein into the vector;

(3) a method of constructing an expression vector capable of being expressed in an eucaryotic cell, by introducing into a vector having a promoter region capable of functioning in an eucaryotic cell, a structural gene of a foreign protein to be governed by the promoter downstream from the promoter region, wherein the rear end of the vector cut at its restriction enzyme recognition site of a sequence -ACATGT- from the 5' direction and the front end of the structural gene of the foreign protein cut at its a restriction enzyme recognition site for a sequence of -N'CATGN- (wherein N is an arbitrary base, and N' is a base complementary to N) are ligated to form a ligation portion having a sequence of -ACATGN-, in which ATG is the translation initiation site for the structural gene of the foreign protein, and the combination of the rear end of the vector cut at its restriction enzyme restriction site and the front end of the structural gene of the foreign protein cut at its restriction enzyme at its recognition site is selected so that the base next to the ATG is an arbitrary base selected from A, T, G, and C;

(4) a *Schizosaccharomyces pombe* transformant carrying the above expression vector; and (5) a method of producing a foreign protein, which comprises culturing the transformant so that the foreign protein is produced and accumulated in the culture medium, and collecting it.

To introduce a structural gene of a foreign protein into a multicloning vector capable of functioning in *S.pombe*, a gene including the structural gene of the foreign protein and the multicloning vector are cut by treating them respectively with restriction enzymes, and then the resulting fragments are ligated to construct an expression vector. In the present invention, the restriction enzyme recognition sites of both of the gene including the structural gene of the foreign protein and the multicloning vector includes ATG. After cutting, the front end (5'-end) of the gene including the structural gene of the foreign protein and the rear end (3'-end) of the multicloning vector are ligated so that ATG present at either end would be the translation initiation site for the structural gene of the foreign protein. For example, when the gene including the structural gene of the foreign protein contain ATG at the front end, the rear end of the anticoding strand of the multicloning vector contains TAC. On the contrary, when the rear end of the multicloning vector contains ATG, the complementary front end of the anticoding strand of the gene including the structural gene of the foreign protein contains TAC.

To make it possible to introduce structural genes of various foreign proteins, it is preferable that the above construction method is applicable even if the base next to the ATG is any of A, T, G and C. Therefore, it is preferred to employ such a method wherein the combination of the restriction cut end of the vector fragment and the restriction cut end of the fragment containing the structural gene of the foreign protein so that the base next to the ATG may be any of A, T, G and C. The multicloning vector to which such a method is applicable and into which various foreign proteins can be introduced, has a multicloning site, which is a site into which a foreign protein is introduced.

In the multicloning vector of the present invention, the restriction enzyme recognition site, to which the structural gene of a foreign protein is introduced, has a sequence of -ACATGT- from the 5' direction. The muticloning vector is cut at the restriction enzyme recognition site by a restriction enzyme that forms the end having the sequence of -A or -ACATG from the 5' direction, and the resulting vector fragment is ligated with a structural gene of a foreign protein having a front end complementary to the rear end of the vector fragment. In these procedures as the restriction enzyme, Afl III or Nsp I is used. The sequence of -ACATGT- may be formed at the ligation site of the vector by modification of vectors having various other ligation sites (for example, by the PCR method).

A structural gene of a foreign protein having a front end complementary to the rear end of the vector fragment is cut out of a gene including the structural gene of the foreign protein by a restriction enzyme which forms a front end complementary to the rear end of the vector fragment having the sequence of -A or -ACATG. The restriction enzyme to cut out the structural gene of the foreign protein is a restriction enzyme which recognizes a restriction enzyme recognition site of -N' CATGN- (wherein N is an arbitrary base, and N' is a base complementary to N) and forms a front cut end having a sequence of CATGN- or N-. As such a restriction enzyme, Nco I, Bsp HI, Afl III, Nsp I or Sph I is used. In the case that the structural gene of the foreign protein does not have such a restriction enzyme recognition site at the front end, such a restriction enzyme recognition site can be provided at the front end of the structural gene of the foreign protein, for example, by site-directed mutagenesis or PCR.

The combination of the rear end of the vector fragment -A and the front end of the structural gene of the foreign protein CATGN-, or the combination of the vector fragment -ACATG and the front end of the structural gene of the foreign protein N- is ligated to form a ligation portion having a sequence of -ACATGN-. In the sequence, ATG corresponds to the translation initiation site for the structural gene of the foreign protein. Whichever the base N next to ATG is, the above-mentioned ligation site can be formed by selecting the combination of the restriction enzymes, and therefore there is no restriction to the structural gene of the foreign protein to be used. As a combination of the restriction enzymes to be used, particularly preferred is the following combinations.

Table 1 shows examples of the combination of a restriction enzyme to cut the vector and a restriction enzyme to cut a gene including the structural gene of a foreign protein which permit the base next to ATG to be any of A, T, G and C. In the combination as the restriction enzyme to cut the vector, Afl III or Nsp I is used, and as the restriction enzyme to cut a gene including the structural gene of a foreign protein, Nco I, Bsp HI, Afl III, Nsp I or Sph I is used. Each of these restriction enzymes are a kind of restriction enzyme that recognizes a palindrome sequence of six bases and cleaves the coding strand within the recognition sequence between the first and the second bases, or between the fifth and the sixth bases from the 5' end, and the anticoding strand between the first and the second bases, or between the fifth and the sixth bases from the 3' end. In this case, as shown by the structures after ligation in Table 1, the sequence of six bases at the ligation site is 5'-ACATGN-3', and by selecting the combination of the restriction enzymes, it is possible to bring any base of A, T, G and C to the position of N next to the translation initiation codon ATG. Also in Table 1 N represents any of A, T, G and C (providing that N in an anticoding strand represents a base complementary to N in the coding strand).

TABLE 1

| Fragment to be ligated | | | The base |
|---|---|---|---|
| Vector side | Insert side | Structure after ligation | next to ATG |
| NNNNA<br>NNNNTGTAC<br>Afl III cut end | CATGGNNNN<br>CNNNN<br>Nco I cut end | Initiation of translation<br>NNNNACATGGNNNN<br>NNNNTGTACCNNNN | G (SEQ ID NO:1) |
| | CATGANNNN<br>TNNNN<br>Bsp HI cut end | Initiation of translation<br>NNNNACATGANNNN<br>NNNNTGTACTNNNN | A (SEQ ID NO:2) |
| | CATGTNNNN<br>ANNNN<br>Afl III cut end | Initiation of translation<br>NNNNACATGTNNNN<br>NNNNTGTACANNNN | T (SEQ ID NO:3) |
| NNNNACATG<br>NNNNT<br>Nsp I cut end | TNNNN<br>GTACANNNN<br>Nsp I cut end | Initiation of translation | |
| | CNNNN<br>GTACGNNNN<br>Sph I cut end | NNNNACATGCNNNN<br>NNNNTGTACGNNNN | C (SEQ ID NO:4) |

The multicloning vector and the expression vector of the present invention has a promoter region which controls the expression of the structural gene of a foreign protein to be introduced (or having been introduced). The promoter governs the expression of the structural gene of the foreign protein introduced downstream. The promoter is capable of functioning in an eucaryotic cell and specifically must function in S.Pombe cells.

The above-mentioned promoter is a promoter that is capable of functioning in S.pombe and accelerates transcription of the structural gene of a foreign protein introduced. As such a promoter, for example, alcohol dehydrogenase gene promoter, human cytomegalovirus gene promoter and human chorionic gonadotropin α gene promoter may be mentioned. Particularly preferred are those strongly accelerate transcription, such as promoters from animal viruses (R. Toyama et al., FEBS Lett, 268,217–221 (1990)). As such a preferable promoter, promoters from animal viruses, particularly human cytomegalovirus gene promoter may be mentioned.

The vector of the present invention may have a drug resistance gene such as an antibiotic resistance gene, a signal peptide-coding gene for secretion of the foreign protein out of the cells and other various genes. Further, it is also possible to make the vector of the present invention a shuttle vector by incorporating a promoter or a drug resistance gene capable of functioning in a procaryotic cell such as E. coli.

An expression vector must have a replication origin in order to be expressed in cells. However, for the multicloning vector and the expression vector of the present invention, it is not always necessary to have a replication origin. A replication origin can be introduced after the expression vector has been constructed. It is also possible of autonomously introduce a replication origin into an expression vector having no replication origin in a cell after the expression vector is taken up by the cell. These methods of introducing a replication origin are already known. For example, a vector having a replication origin capable of functioning in a yeast (hereinafter referred as a yeast vector) can be integrated with the expression vector of the present invention (Japanese Unexamined Patent Publication No. 15380/1993). It is also possible to let the expression vector of the present invention and a yeast vector fuse together in cells autonomously by introducing them into the same cells. Since these method of introducing a replication origin are available, it makes no difference whether the expression vector of the present invention has a replication origin or not. Likewise, it makes no difference whether the multicloning vector of the present invention has a replication origin or not. However, in any case for expression of the expression vector in cells, it is necessary that the vector ultimately has a replication origin.

It is usually essential to introduce a drug resistance gene such as an antibiotic resistance gene into a vector as a marker or for cloning. It is preferred also for the vector of the present invention to have an antibiotic resistance gene and a promoter which accelerates the transcription of the antibiotic resistance gene (hereinafter referred to as a second promoter). The second promoter is preferred to have a transcription accelerating activity lower than the promoter that accelerates the transcription of the above-mentioned structural gene of a foreign protein. As the second promoter, promoters from animal viruses are preferred. Particularly preferred is SV40 early promoter. Although the antibiotic resistance gene governed by the second promoter may be conventional one, particularly in the present invention, neomycin resistance gene is preferred. In the present invention, by the use of the expression vector having an antibiotic resistance gene, it is possible to increase the expression amount of the foreign protein. For this purpose, the transcription accelerating activity of the second promoter must be lower than that of the promoter that governs the structural gene of a foreign protein. For the purpose of explanation, the case of culturing S.pombe that carries an expression vector having SV40 early promoter and neomycin resistance gene governed by the promoter is given as an example. When the S.pombe transformant is cultured in a medium containing G418 (neomycin), the copy number of the expression vector in a cell increases with G418 concentration in the medium. Accordingly, by increasing the G418 concentration, it is possible to increase the copy number of the expression vector in a cell and thereby increase the expression amount of the foreign protein. If the activity of the second promoter is higher than the promoter governing the structural gene of the foreign protein, there is no need to increase the copy number of the expression vector since a small copy number of the vector is enough to induce production of a sufficient amount of neomycin resistance protein (enzyme), and therefore it is impossible to increase the expression amount of the desired foreign protein.

FIG. 4 shows the restriction map of pTL2M, which was prepared in Examples as an example of the multicloning vector of the present invention. The pTL2M is about 5,000 bp (precisely about 5,000±200 bp) in size and has the promoter region of human cytomegalovirus gene (hCMV), an untranslated region (5'-UTR), which connects the promoter region and a multicloning site (MCS), and a MCS for introduction of an structural gene of a foreign protein in this order clockwise. The MCS has the above-mentioned specific restriction enzyme recognition site at its front end. The pTL2M has a SV40 promoter region and neomycin resistance gene ($Nm^R$) in this order counterclockwise from around the front end of the hCMV promoter region. The vector also has ampicillin resistance gene ($Ap_R$), which is a drug resistance gene capable of functioning in procaryotic cells such as E.coli, downstream from $Nm^R$. Further as illustrated, it has two SV40 terminators, a replication origin capable of functioning in procaryotic cells and a downstream untranslated region (3'-UTR).

The untranslated region (5'-UTR) is a sequence between the rear end of the promoter region (which usually has a sequence of TATA) and the translation initiation codon ATG. The length of the untranslated region often affects the translation activity. The untranslated region in the vector of the present invention is preferably from 20 to 200 bp long, more preferably from 30 to 100 bp long. In pTL2M illustrated, the region is about 56 bp long.

The pTL2M as illustrated has no replication origin capable of functioning in eucaryotic cells. When the pTL2M is used, it is necessary to introduce a replication origin capable of functioning in eucaryotic cells into it. Sequences containing a replication origin capable of functioning in eucaryotic cells and vectors containing such sequences are already known, and a replication origin can be introduced into pTL2M by using such a vector. As known vectors containing a replication origin capable of functioning in S.pombe cells, pAU5 and pAL7 may, for example, be mentioned (K. Okazaki et.al., Nucleic Acids Research, Vol. 18,6485–6489(1990), K. Okayama et al., Molecular Cellular Biology, Vol. 3, 280–289, (1983)). These yeast vectors contain an autonomously replicating sequence (ars) and a stabilizing sequence (stb) and further carry a selective marker or an antibiotic resistance gene. By incorporating such a yeast vector into pTL2M, a multicloning vector capable of replicating in S.Pombe can be obtained. Likewise, by incorporating such a yeast vector into a expression vector which is prepared by introducing a structural gene of a foreign protein into the multicloning vector, an expression vector capable replicating in S.pombe cells can be obtained. The method of constructing an expression vector by incorporation of a yeast vector is disclosed in Japanese Unexamined Patent Publication No. 15380/1993 concerning an invention by the present inventors, as well as the above-mentioned references.

In general, introduction of a large vector into cells often involves difficulty. The pTL2M itself is a relatively large vector, and therefore it is considerably difficult to introduce pTL2M having been integrated with a yeast vector into yeast cells. As a method of overcoming such difficulty, a method wherein the above-mentioned yeast vector (which is usually cut by a restriction enzyme and used in the form of linear DNA) and the multicloning vector or the expression vector of the present invention are introduced into the same cell. In this case, the yeast vector is automatically integrated with the multicloning vector or the expression vector to automatically form a vector containing a replication origin as mentioned above. In examples described later, S.Pombe was transformed by this method.

The general technique of constructing a multicloning vector or an expression vector is already known and disclosed, for example, in a reference, J. Sambrook et al., "Molecular Cloning 2nd ed.", Cold Spring Harbor Laboratory Press (1989). The multicloning vector and the expression vector of the present invention can be constructed by the above-mentioned method by using this conventional technique. As a strain of S.pombe to be used in the present invention as a host of the expression vector, ATCC 38399 (leu1-32h-) and ATCC 38436 (ura4-294h-) may, for example, be mentioned. These strains are available from American Type Culture Collection.

S.pombe can be transformed by using an expression vector by known methods, and a S.pombe transformant can be obtained by, for example, the lithium acetate method (K. Okazaki et al., Nucleic Acids Res., 18, 6485–6489 (1990).). The transformant is cultured in a known medium, and nutrient media such as YPD medium (M. D. Rose et al., "Methods In Yeast Genetics", Cold Spring Harbor Laboratory Press (1990).), minimal media such as MB medium (K. Okazaki et al., Nucleic Acids Res., 18, 6485–6489 (1990)) and the like may be used. The transformant is cultured usually at from 16° to 42° C., preferably at from 25° to 37° C., for from 8 to 168 hours, preferably from from 48 to 96 hours. Either of shaking culture and stationary culture can be employed, and, if necessary, the culture medium may be stirred or aerated.

As methods of isolating and purifying the protein produced in the culture, known methods, such as methods utilizing difference in solubility such as salting out and precipitation with a solvent, methods utilizing difference in molecular weight such as ultrafiltration and gel electrophoresis, methods utilizing difference in electric charge such as ion-exchange chromatography, methods utilizing specific affinity such as affinity chromatography, methods utilizing difference in hydrophobicity such as reverse phase high performance liquid chromatography, and methods utilizing difference in isoelectric point such as isoelectric focusing may be mentioned.

The isolated and purified protein can be identified by conventional methods such as westernblotting or assay of its activity. The structure of the purified protein can be defined by amino acid analysis, amino-terminal analysis, primary structure analysis and the like.

BRIEF DESCRIPTION OF DRAWINGS

The accompanying drawings in association with the item best mode for carrying out the invention, except FIG. 4, which has been already explained, are explained below.

FIGS. 5 to 11 are concerned in Example 5. FIG. 5 illustrates the structure of the expression vector pTL2L constructed in Example 5. FIG. 6 shows SDS-PAGE and westernblotting patterns which demonstrate expression of human lipocortin I. FIG. 7 is a SDS-PAGE pattern of purified human lipocortin I. FIG. 8 is a graph showing the PLA2 inhibitory activity of human lipocortin I. FIG. 9 is an SDS-PAGE pattern showing the actin binding activity of human lipocortin I. FIG. 10 is an HPLC elution pattern obtained by amino acid analysis of human lipocortin I. FIG. 11 is a graph showing the variation of the copy number of pTL2L.

BEST MODE OF CARRYING OUT THE INVENTION

Now, the present invention will be described in further detail with reference to Examples. However, it should be understood that the technical scope of the present invention is by no means restricted to such specific examples.

Example 1 demonstrates preparation of vector pRL2M, the base of the vector is the present invention, and Example 2 demonstrates preparation of vector pTL2M, which has no structural gene of a foreign protein introduced thereto, by using pRL2M. This vector pTL2M is a multicloning vector of the present invention. The other Examples are Examples of introduction of structural genes of various foreign proteins into the vector pTL2M and the tests for their expression. Example 3 demonstrates preparation of a S.pombe transformant containing the vector pTL2M, and Example 4 demonstrates preparation of the extract from the transformant cells (for use as control). Example 5 shows specifically, various tests on production of human lipocortin I.

EXAMPLE 1
Preparation of vector pRL2M

A plasmid pcD4B having been prepared by the known method (see Japanese Unexamined Patent Publication No. 15380/1993) was digested with a restriction enzyme Sac I, and the ends of the resulting fragment were blunted with T4 DNA polymerase. It was further digested with a restriction enzyme Bam HI, and then the nucleic acid fraction was collected by phenol extraction and ethanol precipitation. Then, the fraction was subjected with agarose gel electrophoresis, and then the DNA fragment of about 4,500 bp was purified by the glass beads method (by using DNA PREP (tradename) manufactured by Asahi Glass Company Ltd.; thereafter, purification by the glass beads method was conducted in the same manner).

On the other hand, a vector pcD41ipo I including human lipocortin I gene (cDNA), which had been prepared by the known method (Japanese Unexamined Patent Publication No. 15380/1993), was digested with restriction enzymes Xmn I and Bam HI, and then the nucleic acid fraction was collected by phenol extraction and ethanol precipitation. The fraction was subject to the agarose gel electrophoresis, and the DNA fragment of about 1,300 bp was purified by the glass beads method.

Figure 1:
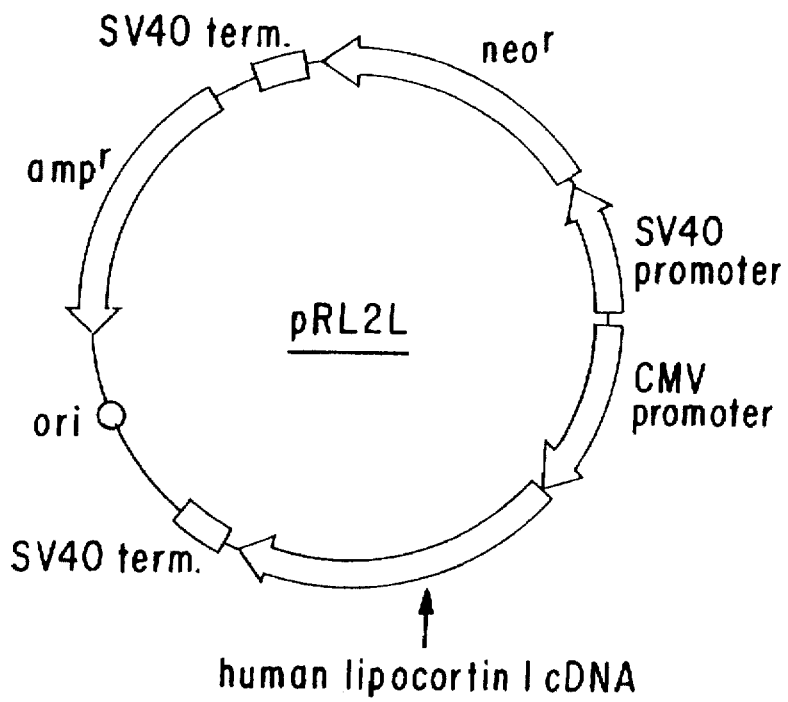
FIG. 1 and FIG. 2 illustrate the structures of the vector pRL2L and the vector pRL2M, which were constructed in Example 1.

The two DNA fragments were ligated by using the ligation kit (sold by the Takara Shuzo Co.), and *Escherichia coli* DH5 (sold by Toyobo Co.) was transformed with it. From the resulting transformants, vectors were prepared, the transformant carrying the desired vector pRL2L (FIG. 1) was screened out. Vector pRL2L thus obtained was confirmed to be the desired vector by partial base sequencing and preparing the restriction map.

The lipocortin I expression vector pRL2L was digested by restriction enzymes EcoRI and Hid III. After phenol extraction and ethanol precipitation, it was subjected to agarose gel electrophoresis. The band corresponding to a fragment of about 5,000 bp was cut out, and the fragment was purified by the glass beads method. Separately, a known plasmid pUC 19 was digested with restriction enzymes Eco RI and Hid III. After phenol extracted and precipitation ethanol, it was subjected to polyacrylamide gel electrophoresis. The band corresponding to a fragment of about 60 bp was cut out, and the fragment was isolated from the gel by extraction.

Figure 2:
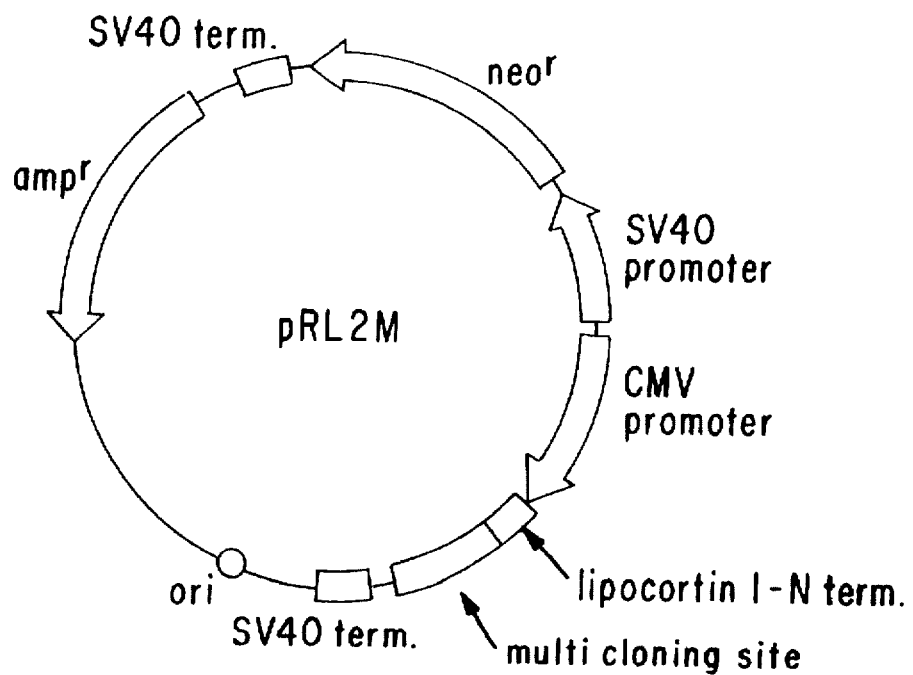

The two fragments were ligated, and *Escherichia coli* DH5 was transformed by using it to screen out the desired vector pRL2L (FIG. 2). It was confirmed to the desired vector by partial DNA sequencing and preparation of the restriction map.

EXAMPLE 2
Preparation of a vector pTL2M

The desired fragment was amplified by PCR by using Taq polymerase, pRL2M as a template, and oligodeoxyribonucleotides 5'-TTGACTAGTTATTAATAGTA-3'(SEQ ID NO:5) and 5'-CTAGAATTCACATGTTTGAAAAAGTGTCTTTATC-3'(SEQ ID NO:6) as synthetic primers. The terminals of the desired fragment was modified by using restriction enzymes Spe I and Eco RI, and the fragment was extracted with phenol, precipitated with ethanol, subjected with agarose gel electrophoresis. The band corresponding to a fragment of about 600 bp was cut out, and the fragment was purified by the glass beads method.

Figure 3:
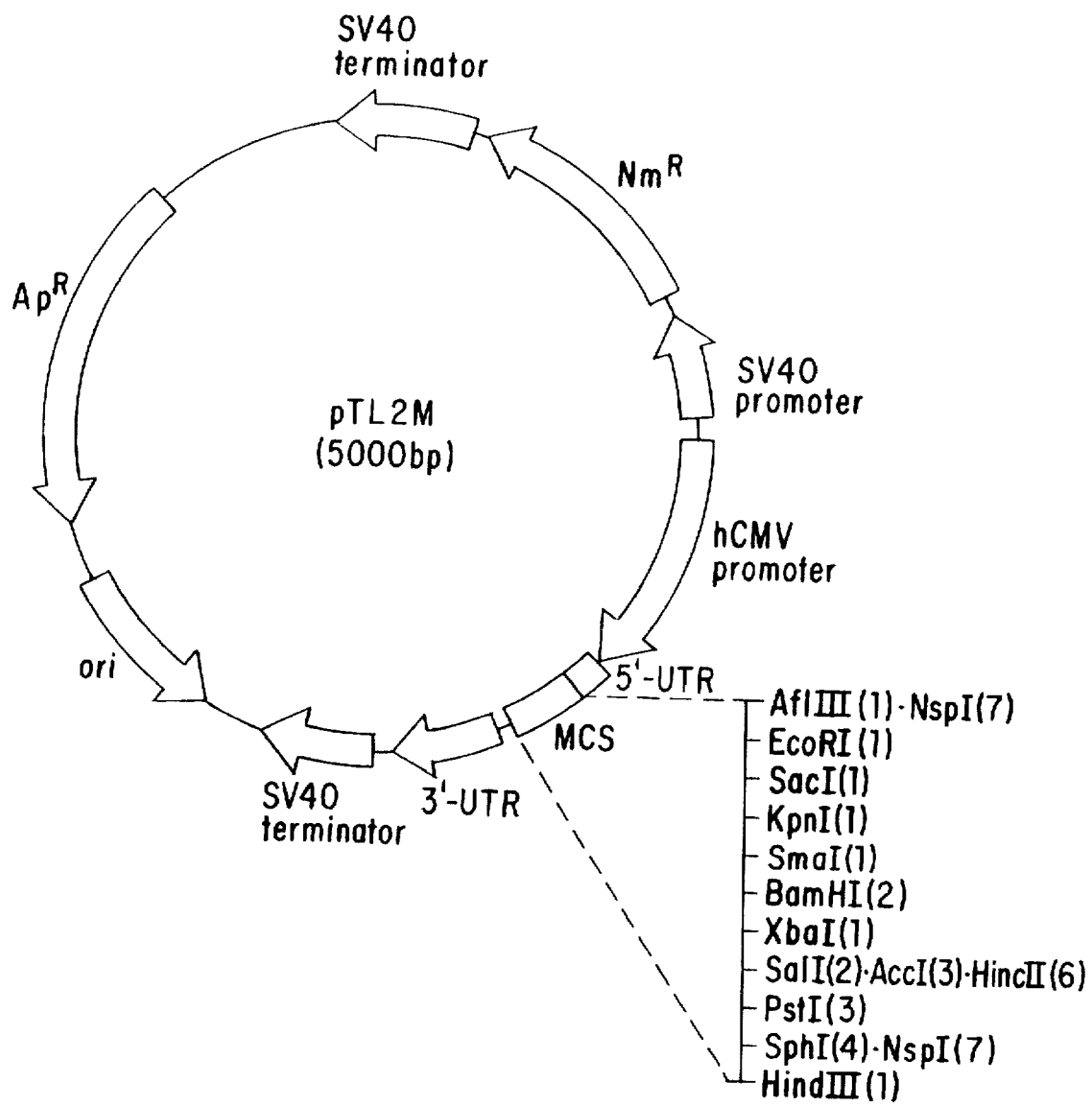
FIG. 3 illustrates the structure of pTL2M, the multicloning vector of the present invention constructed in Example 2
Figure 4:
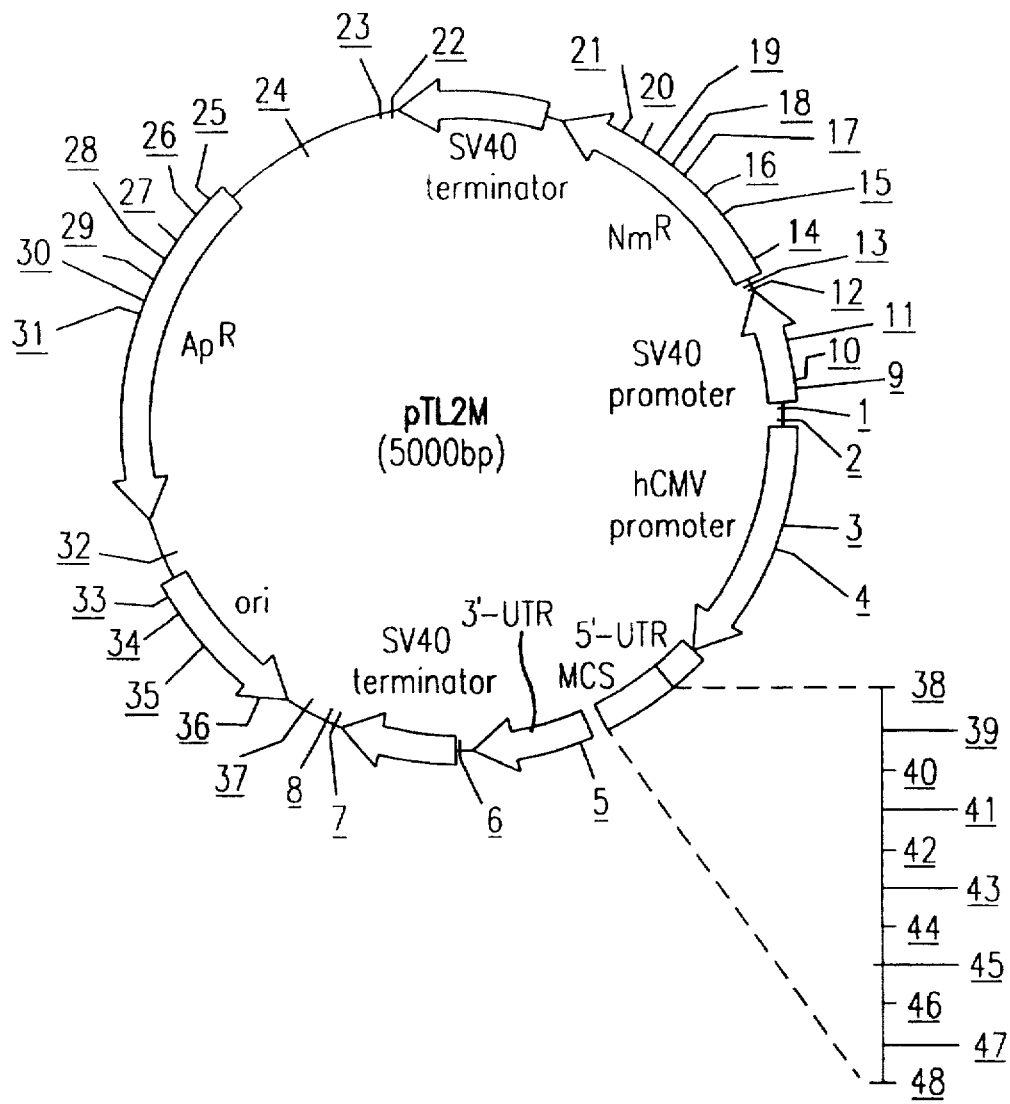
FIG. 4 is the restriction map of pTL2M.

Separately, pRL2M was digested by restriction enzymes Spe I and Eco RI, extracted with phenol, precipitated with ethanol, and subjected to agarose gel electrophoresis, and the band corresponding to a fragment of about 4,500 bp was cut out, and the fragment was purified by the glass beads method. The two fragments were ligated, and *Escherichia coli* DH5 was transformed by using it to screen out the desired vector pTL2M (FIG. 3). The vector screened out was confirmed to be the desired vector by partial DNA sequencing and preparation of the restriction map. FIG. 4 is the restriction map of pTL2M.

EXAMPLE 3
Introduction of pTL2M into a yeast

The leucine-requring strain of *S.pombe*, ATCC 38–399 (leu1 -32 h-) was grown in a minimal medium until the cell number became $0.8 \times 10^7$ cells/ml. The cells were collected, washed, and suspended in 0.1M lithium acetate (pH 5.0) so that the cells number would be $10^9$ cells/ml. It was incubated at 30° C. for 60 minutes. 1 μg of the pAL7 DNA cut by Pst I and 2 μg of pTL2M obtained in Example 1 were dissolved in 15 μl of TE (Tris buffer containing EDTA). The resulting solution was added to 100 μl of the suspension, and then 290 μof 50% PEG 4,000 was added, and they were mixed enough. Then, the mixture was incubated at 30° C. for 60 minutes, at 43° C. for 15 minutes, and at room temperature for 10 minutes in this order. After removal of PEG 4,000 by centrifugation, the cells were suspended in 1 ml of the culture medium.

A 100 μl portion of the cell suspension was taken out, and 900 μl of culture medium was added to it and incubated at 32° C. for 30 minutes. 300 μl of the cell culture was spread on minimal agar medium, and it was incubated at 32° C. for 3 days. The transformants were transferred to plates containing G418 and cultured at 32° C. for 5 days. The transformant thus obtained was the desired transformant.

EXAMPLE 4
Culture of the transformant and preparation of the cell extract

The transformant obtained in Example 3 was cultured in 50 ml of a liquid medium containing 2% glycose, 1% yeast extract, 2% peptone and 200 μg/ml of G 418 at 32° C. for 3 days. From the medium, about $10^8$ cells was collected, washed and suspended in 50 mM Tris-HCl buffer (pH 7.5). The suspension was subjected to sonication and centrifugation to obtain the cell extract (the supernatant). The cell extract was used as the control in analysis by SDS-polyacrylamide gel electrophoresis (4–20% polyacrylamide gel, manufactured by TEFCO, hereinafter referred to as SDS-PAGE) in the following examples.

EXAMPLE 5
Expression of human lipocortin I

PCR by Taq polymerase was conducted by using a known vector pcD4lipo I containing the whole lipocortin I cDNA (Japanese Unexamined Patent Publication No. 15380/1993) as a template and polyoligodeoxyribonucleotides 5'-ATGCCATGGCAATGGTATCAGAATT-3'(SEQ ID NO:7) and 5'-AGCCAGTATACACTCCGCTA-3'(SEQ ID NO:8) as synthetic primers to amplify the desired fragment. The fragment was treated with restriction enzymes Nco I and Bam HI for its terminal modification, extracted with phenol, precipitated with ethanol, and subjected to agarose gel electrophoresis. The band corresponding to the fragment of about 1,400 bp was cut out, and the fragment was purified by the glass beads method.

Figure 5:
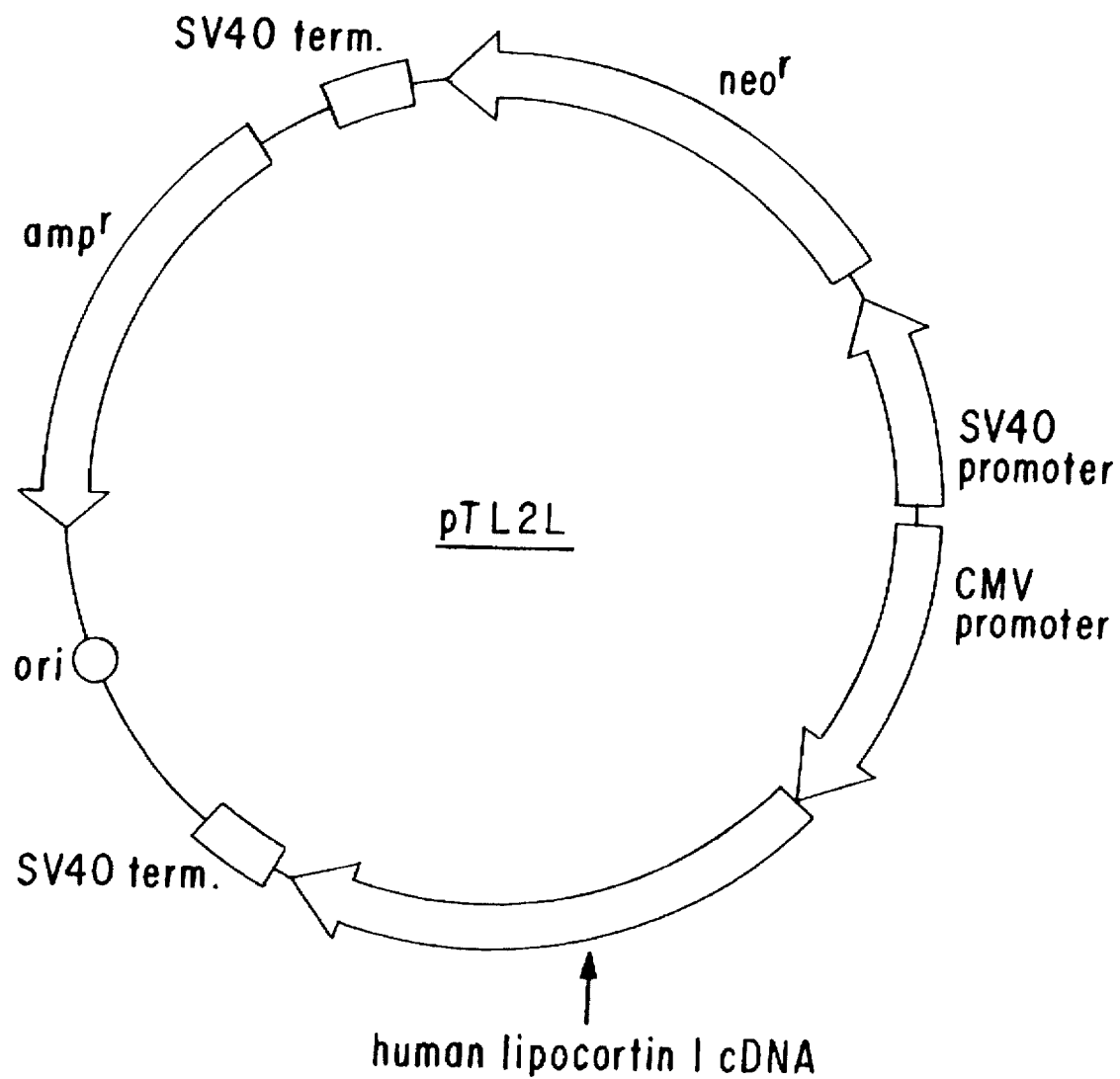

Separately, pTL2M was digested by restriction enzymes Afl III and Bam HI, extracted with phenol, precipitated with ethanol, and then subjected to agarose gel electrophoresis. The band corresponding to a fraction of about 5,000 bp was cut out, and the fragment was purified by the glass beads method. The both fragments were ligated, and *Escherichia coli* DH5 was transformed by using it to screen out the desired vector pTL2L (FIG. 5). The obtained vector was confirmed to be the desired vector by partial DNA sequencing and preparation of the restriction map.

Figure 6:
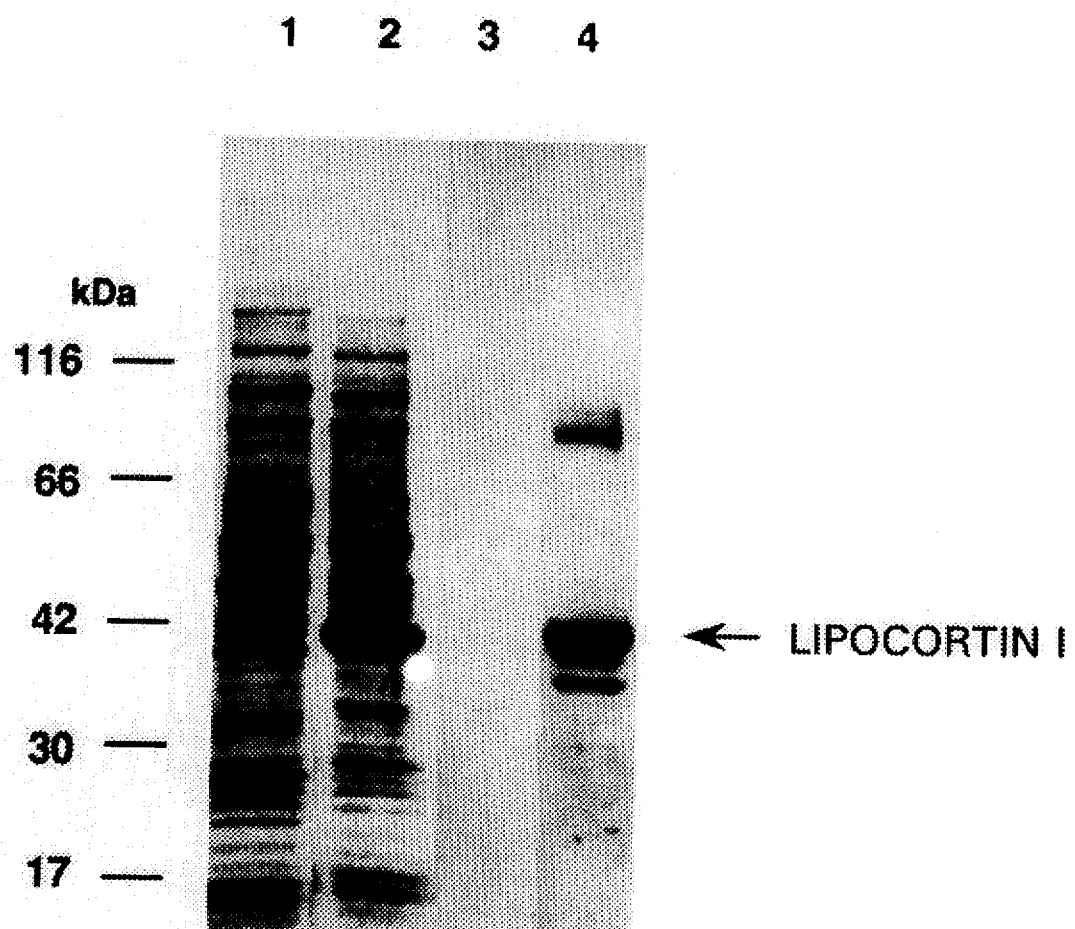
Figure 7:
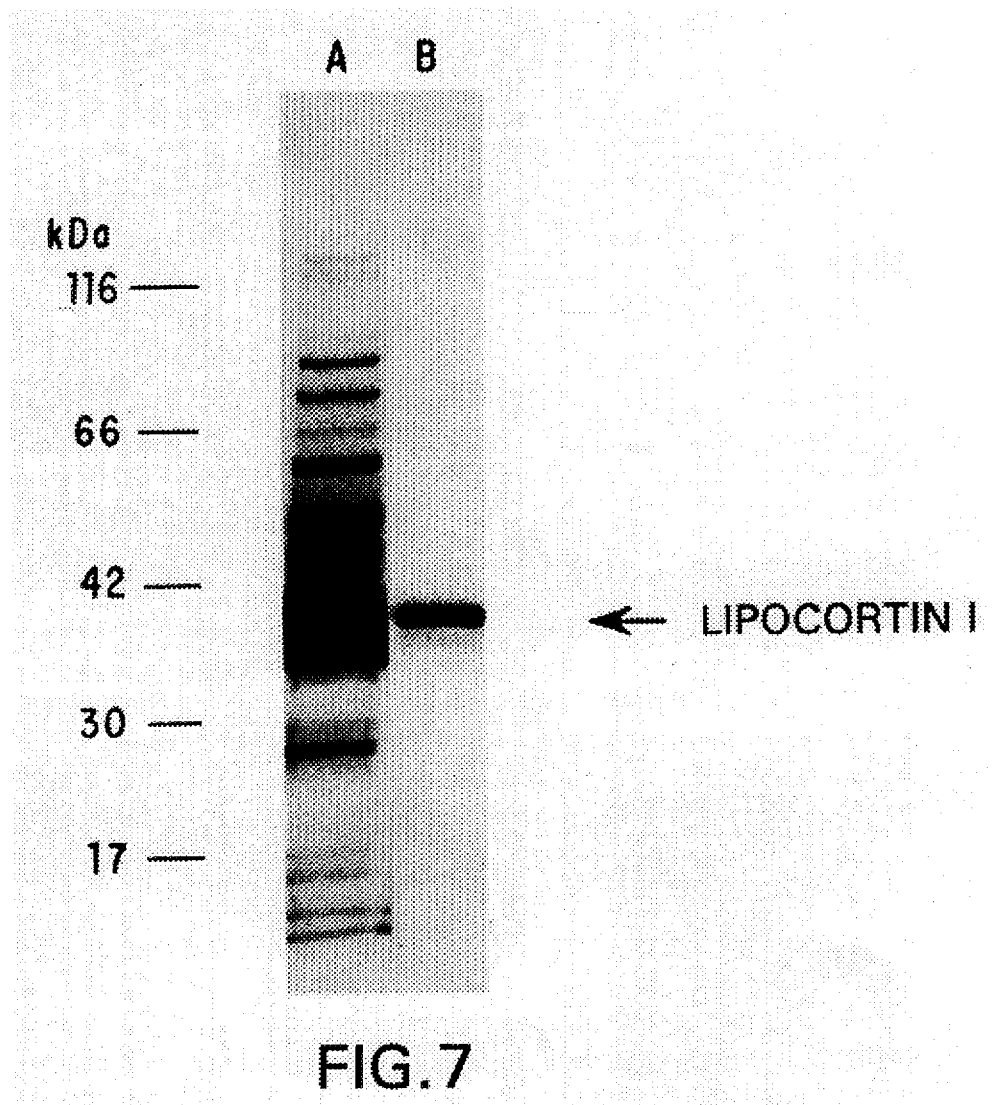

*S.pombe* was transformed with the vector in the same manner as in Example 3 and its cell extract was prepared in the same manner as in Example 4 in the presence of proteases (12 μM PMSF, 25 μM leupeptin and 5 μM E-64). The cell extract was analyzed by SDS-PAGE, and at the position corresponding to molecular weight of 36,000, a band which was not detected for the cell extraction from the control pTL2M-introduced yeast, was detected. As a result of westernblotting by using anti-human lipocortin I antibody (rabbit), the band was specifically stained (FIG. 6). FIG. 6 is the SDS-PAGE and westernblotting patterns that indicate the expression of human lipocortin I. In FIG. 6, A to D represent the followings:

A; *S.pombe* (pTL2M) cell extract
B; *S.pombe* (pTL2L) cell extract
C; *S.pombe* (pTL2M) cell extract
D; *S.pombe* (pTL2L) cell extract Quantitative westernblotting analysis was conducted by using $^{125}$I-protein A as the secondary antibody and native lipocortin I as a standard, and as a result, it was found that the expressed lipocortin accounted for 50 wt % of all the soluble protein. Purification of the human lipocortin I expressed in the fission yeast The crude extract obtained above was applied to an affinity column having an monoclonal antibody that recognizes calcium-bonded human lipocortin I as the ligand under conditions of 1 mM $CaCl_2$, 50 mM Tris-HCl (pH 7.5) and 0.15M NaCl to allow the human lipocortin I in the crude extract to be absorbed on the column. The recombinant human lipocortin I was eluted with 50 mM Tris-HCl (pH 7.5) containing 2 mM EGTA and 0.15M NaCl. The recombinant human lipocortin I thus eluted showed a single band upon SDS-PAGE analysis (FIG. 7). FIG. 7 is the SDS-PAGE pattern that demonstrates purification of the human lipocortin I. In FIG. 7, A and B represent the following:

A; *S.pombe* (pTL2L) crude extract
B; purified human lipocortin I

Phospholipase A2 (PLA2)-inhibitory activity

Figure 8:
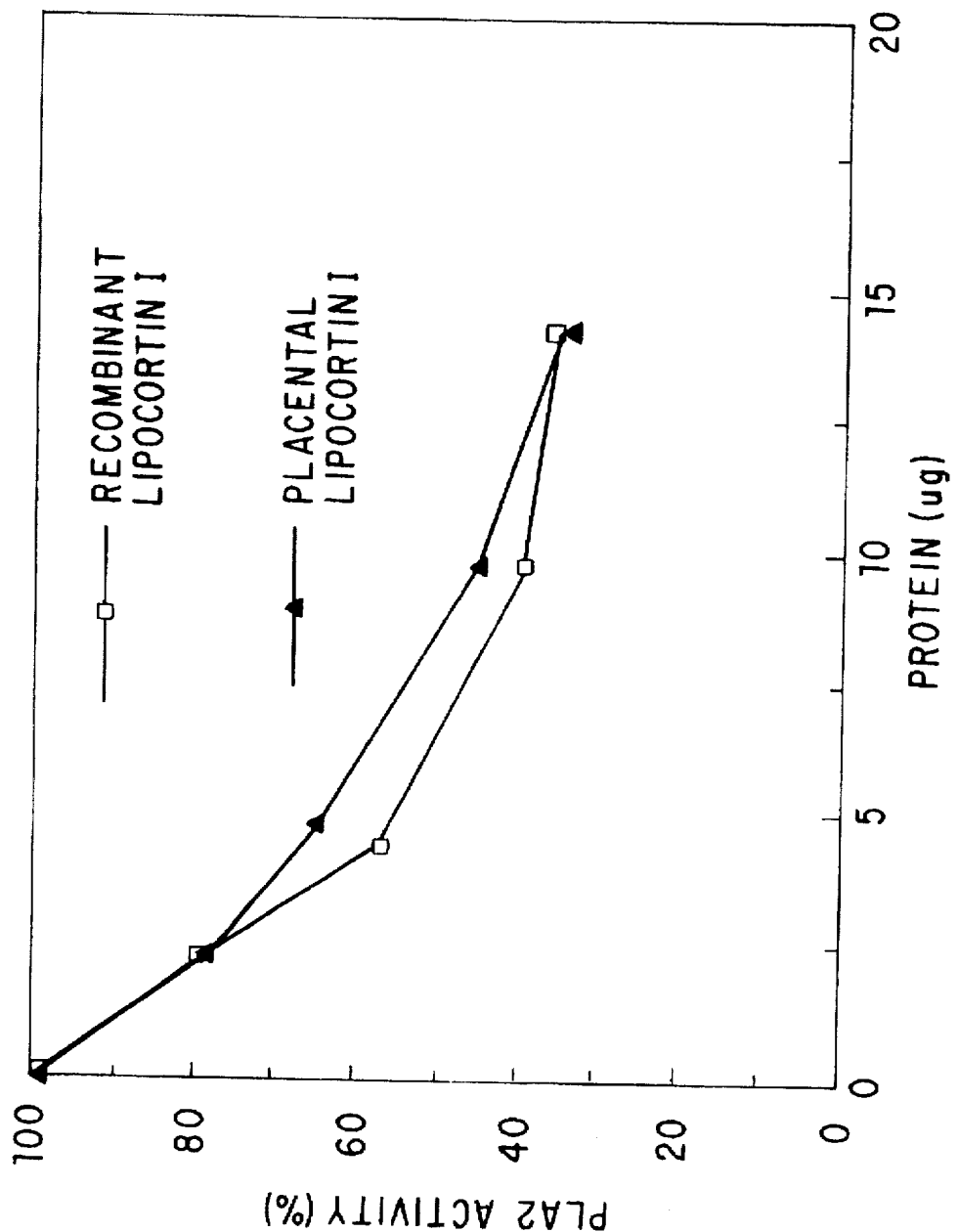

The PLA 2 inhibitory activity of the recombinant human lipocortin I thus purified was measured according to the method of Rothhut, B. et al. (Rothhut B., et al., (1983) Biochem. Biophys. Res. Commun. 117, 878–884). The inhibitory activity of the human lipocortin I against bee toxin PLA 2 was measured by using *Escherichia coli* labeled with oleic acid containing trithium. The results are shown in FIG. 8. The results show that the recombinant human lipocortin I is similar to human placental lipocortin I in inhibitory activity, the degree of inhibition, the mode of inhibition.

FIG. 8 is a graph which shows a relationship between the weight of the protein and the PLA 2 activity. F-actin binding activity.

Figure 9:
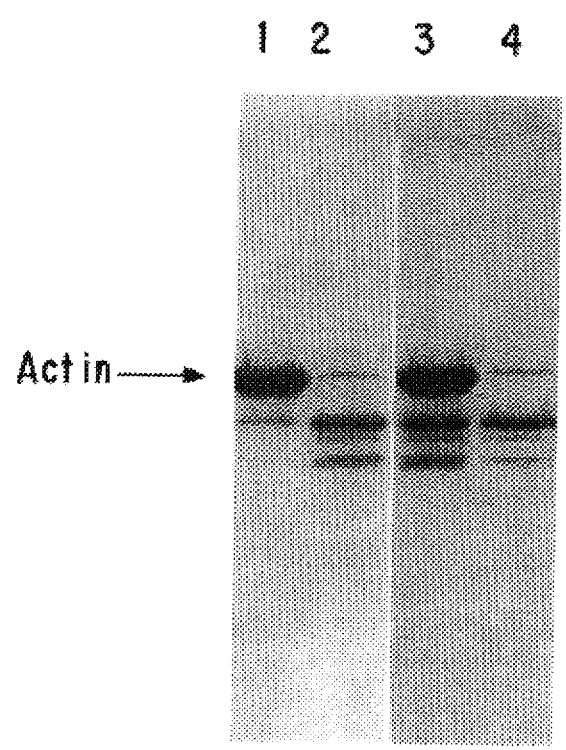

Binding of the human lipocortin I thus purified to F-actin in the presence of calcium was examined by the method of Hayashi, H et al. (Hayashi, H. et al. (1987) Biochem. Biophys. Res. Commun. 146, 912–919). Like human placental lipocortin I, 50 wt % of the recombinant human lipocortin I bound to F-actin in the presence of 1 mM calcium, and no binding was observed in the presence of 1 mM EGTA (FIG. 9). FIG. 9 is a SDS-PAGE pattern showing actin binding activity. In FIG. 9, 1 to 4 represents the followings:

1; centrifugal residue in the presence of 1 mM EGTA,
2; centrifugal supernatant in the presence of 1 mM EGTA,
3; centrifugal residue in the presence of 1 mM $CaCl_2$,
4; centrifugal supernatant in the presence of 1 mM $CaCl_2$.

Amino acid composition

The amino acid composition of the recombinant human lipocortin I thus obtained was analyzed by means of an amino acid analyzer (JEOL JLC-360). The results are shown in Table 2. The amino acid composition was found to be consistent with that expected from the DNA base sequence.

TABLE 2

| Amino acid | Number of amino acid reside per molecule | |
| --- | --- | --- |
| | Experimental value | Theoretical value |
| Asx | 39.4 (39) | 39 |
| Thr | 20.2 (20) | 22 |
| Ser | 19.2 (19) | 19 |
| Glx | 40.3 (40) | 39 |
| Gly | 23.0 (23) | 20 |
| Ala | 34.0 (34) | 33 |

TABLE 2-continued

| Amino acid | Number of amino acid reside per molecule | |
|---|---|---|
| | Experimental value | Theoretical value |
| Val | 18.0 (18) | 19 |
| Met | 5.7 (6) | 8 |
| Ile | 19.9 (20) | 21 |
| Leu | 34.9 (35) | 34 |
| Tyr | 10.7 (11) | 11 |
| Phe | 10.7 (11) | 11 |
| His | 6.2 (6) | 5 |
| Lys | 32.3 (32) | 32 |
| Arg | 17.6 (18) | 19 |
| Pro | 8.0 (8) | 8 |
| Trp | n.d. | 1 |
| Cys | n.d. | 4 |
| Total | (340) | 345 |

Amino acid sequence at the amino-terminal

The determination of the amino acid sequence at the amino terminal of the recombinant human lipocortin I thus obtained was tried by using a vapor phase sequencer (SHIMADZU PSQ-1), however, no PTH-amino acid was detected. Then, the recombinant human lipocortin I was hydrolyzed thoroughly by V8 protease (Boehringer), and the resulting fragments were fractionated by HPLC on an ODS C18 column. The amino acid composition of each fragment was analyzed, whereupon the amino-terminal fragment was selected. Then, the amino-terminal fragment peptide was treated with an acylamino acid releasing enzyme. The results are shown in FIG. 10.

FIG. 10 shows elution patterns by HPLC. FIG. 10a is a graph showing the eluted amount of the amino-terminal fragment, and FIG. 10b is a graph showing the eluted amount of the acylamino acid releasing enzyme-treated amino-terminal fragment. FIG. 10b shows appearance of a peak at a short retention time and the shift of the peak for the amino-terminal fragment.

Figure 11:
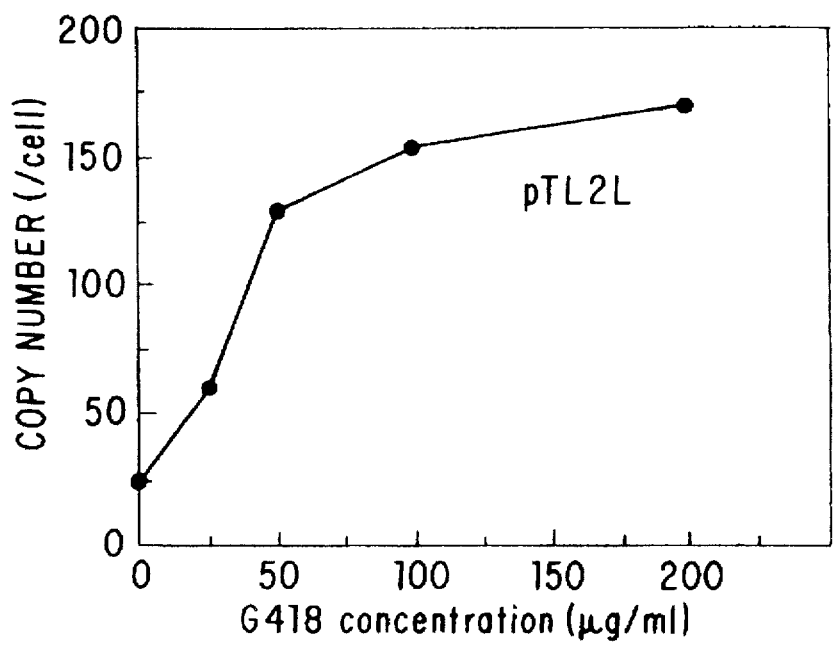

The fraction at the former peak was collected and hydrolyzed, and its amino acid composition was analyzed, whereupon it was found that a peak corresponded to Ala. HPLC of acetyl Ala gave a peak at the same position (FIG. 10b). The fragment in the fraction at the latter peak was analyzed by the sequencer and found to have a sequence of Met-Val-Ser-Glu (SEQ ID NO:15). It is concluded that the recombinant human lipocortin I had an amino acid sequence of Acetyl-Ala-Met-Val-Ser-Glu at its amino terminal, similarly to the native form. Determination of the copy number of the human lipocortin I expression vector The transformant obtained in Examples was cultured in the same manner as in Example 4 except that five different media with G418 concentrations of 0, 25, 50, 100 and 200 μg/ml were used, to obtain 5×10⁷ cells from each medium. The cells were crushed by using glass beads, SDS and phenol to extract the whole DNA. The whole DNA was digested by restriction enzymes Eco RI and Hind III, subjected to 0.8% agarose gel electrophoresis, transferred to nylon membranes, and southern hybridization was performed by using a Eco RI-Hind III fragment of human lipocortin I gene as a probe. The results are shown in FIG. 11. FIG. 11 is a graph showing the relationship between the G418 concentration and the copy number of pTL2L. FIG. 11 shows that the copy number of the vector in a cell increases to the maximum of about 200 copies, depending upon the G418 concentration in the medium.

EXAMPLE 6
Expression of rat arginase

From the vector pARGr-2 including the whole rat liver arginase cDNA, given by professor Masataka Mori at the medical department of Kumamoto University [S.Kawamoto et al., Biochem. Biophys. Res, Commun., 136, 955–961 (1986)], an insert was cut out with restriction enzymes Eco RI and Pst I and subcloned into the Eco RI-Pst I site in a commercially available vector Bluescript.

PCR by Taq polymerase was conducted by using the vector as the template, oligodeoxyribonucleotides 5'-GACTCATGAGCTCCAAGCCAAAGCC-3'(SEQ ID NO:9) and 5'-TTCCCAGTCACGACGTTGTA-3'(SEQ ID NO:10) as synthetic primers to amplify the desired fragment. After terminal modification by restriction enzymes Bsp HI and Xba I, phenol extraction, and ethanol precipitation, it was subjected to agarose gel electrophoresis. The band corresponding to a fragment about 1,300 bp was cut out, and the desired fragment was purified by the glass beads method.

Figure 12:
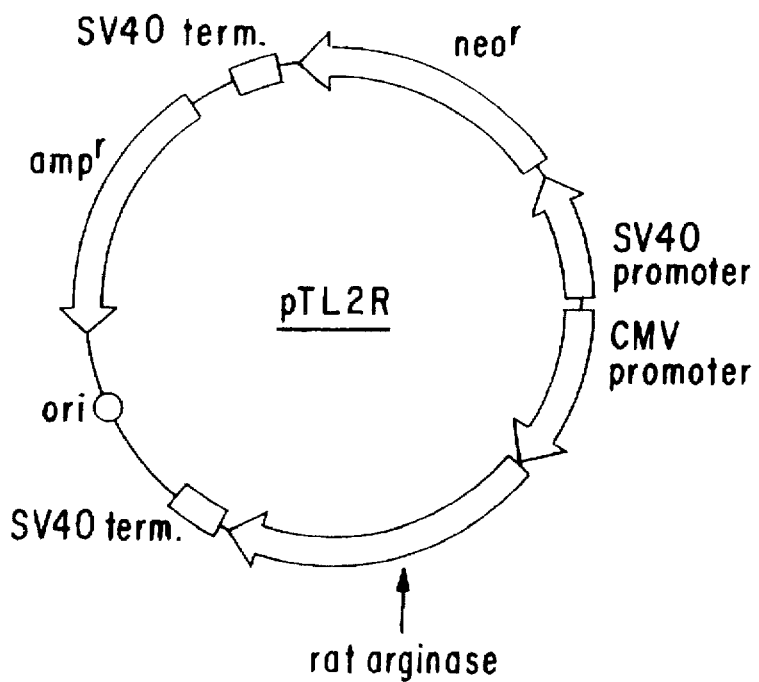
FIG. 12 illustrates the structure of the expression vector pTL2R constructed in Example 6.

Separately, pTL2M as digested with restriction enzymes Afl III and Xba I, and after phenol extraction and ethanol precipitation, it was subjected agarose gel electrophoresis. The band corresponding a fragment of about 5,000 bp was cut out and the fragment was purified by the glass beads method. The two fragments were ligated, Escherichia coli DH5 was transformed with it to screen out the desired vector pTL2R (FIG. 12). The screened vector was confirmed to be the desired vector by partial base sequencing and preparation of the restriction map.

S.pombe was transformed with the vector in the same manner as in Example 3, and the cell extract was prepared in the same manner as in Example 4. SDS-PAGE was performed to confirm the expression of rat arginase, and a clear band, which was not detected in the case of the control pTL2M, was detected at the position corresponding to the molecular weight of rat arginase, about 35,000. The expression amount of rat arginase was measured by a densitometer and found to be from 30 to 50 wt % of the total cell protein. The protein corresponding to the band was confirmed to be rat arginase by westernblotting using an antibody specific to rat arginase. EXAMPLE 7
Expression of human IL-6

PCR using Taq polymerase was conducted by using a known vector pUC 19 including the whole human IL-6 cDNA as a template and oligodeoxyribonucleotides 5'-ATCGCATGCCAGTACCCCCAGGAGAAGA-3'(SEQ ID NO:11) and 5'-TGAAAATCTTCTCTCATCCG-3'(SEQ ID NO:12) as synthetic primers to amplify the desired fragment. After terminal modification by restriction enzymes Sph I and Hind III, phenol extraction and ethanol precipitation, it was subjected to agarose gel electrophoresis. The band corresponding to a fragment of about 1,000 bp was cut out, and the fragment was purified by the glass beads method.

Figure 13:
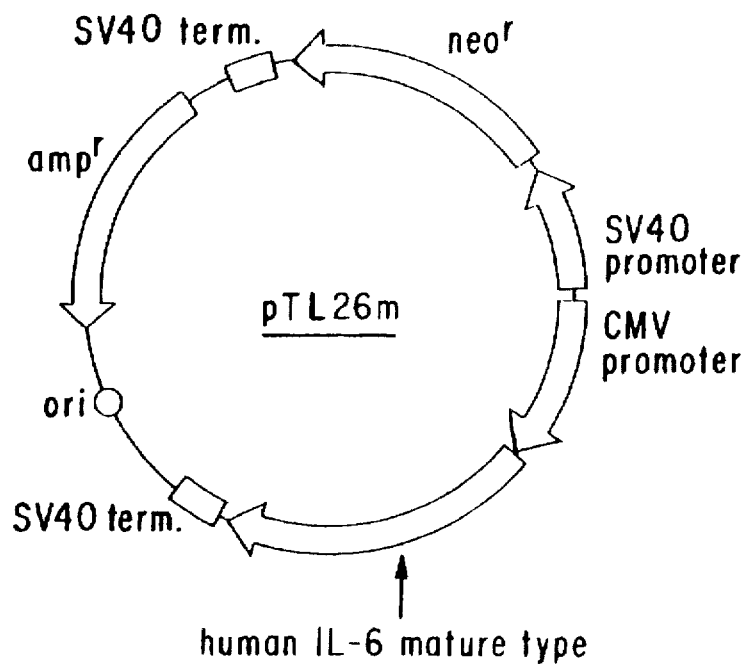
FIG. 13 illustrates the structure of the expression vector pTL26m constructed in Example 7.

Separately, pTL2M was digested by restriction enzymes Afl III and Hind III, and after phenol extraction and ethanol precipitation, it was subjected to agarose gel electrophoresis. The band corresponding to a fragment of about 5,000 bp was cut out, and the fragment was purified by the glass beads method. The two fragments were ligated, and Escherichia coli DH5 was transformed with it to screen out the desired vector pTL26 m (FIG. 13). The screened vector was confirmed to be the desired vector by partial base sequencing and preparation of the restriction map. S.pombe was transformed in the same manner as in Example 3, and the cell extract was prepared in the same manner as in Example 4. SDS-PAGE was performed to confirm the expression of human IL-6 and as a result, a clear band which was not detected in the case of the control pTL2M, was detected at the position corresponding to the molecular weight of human IL-6, about 21,000. The expression amount was measured by a densitometer and found to be about 10 wt % of the total cell protein. The protein corresponding to the band was confirmed to be human IL-6 by westernblotting using an antibody specific to human IL-6.

EXAMPLE 8
Expression of rat NDP kinase a form

A vector including the whole cDNA of rat NDP kinase a form, pNDPKα which was given by Dr. Narimichi Kimura, at Metropolitan gerontologic research institute, was digested by restriction enzymes Nco I and Hind III. After phenol extraction and ethanol precipitation, it was subjected to agarose gel electrophoresis. The band corresponding to a fragment of about 600 bp was cut out, and the fragment was purified by the glass beads method. Separately, pTL2M was digested by restriction enzymes Afl III and Hind III, and after phenol extraction and ethanol precipitation, it was subjected to agarose gel electrophoresis. The band corresponding to a fragment to about 5,000 bp was cut out, and the fragment was purified by the glass beads method.

Figure 14:
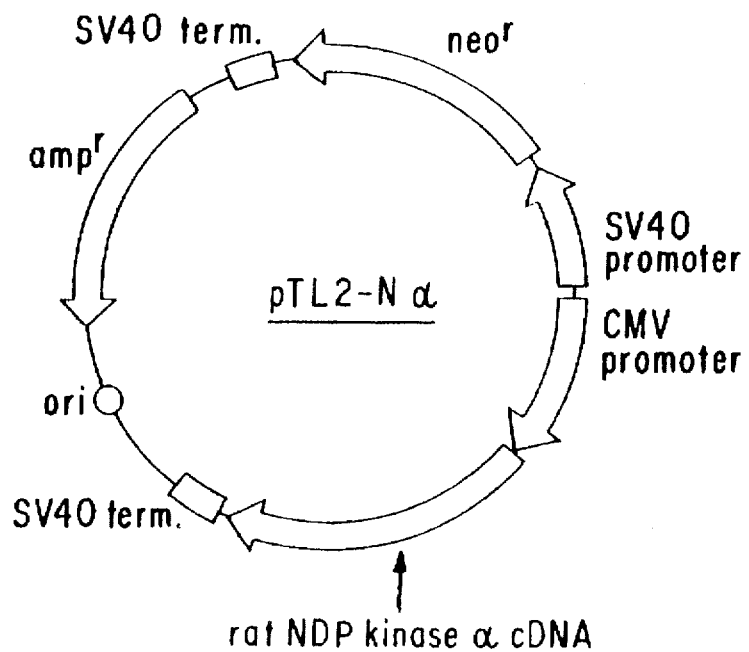
FIG. 14 illustrates the structure of the expression vector pTL2Nα constructed in Example 8.
Figure 15:
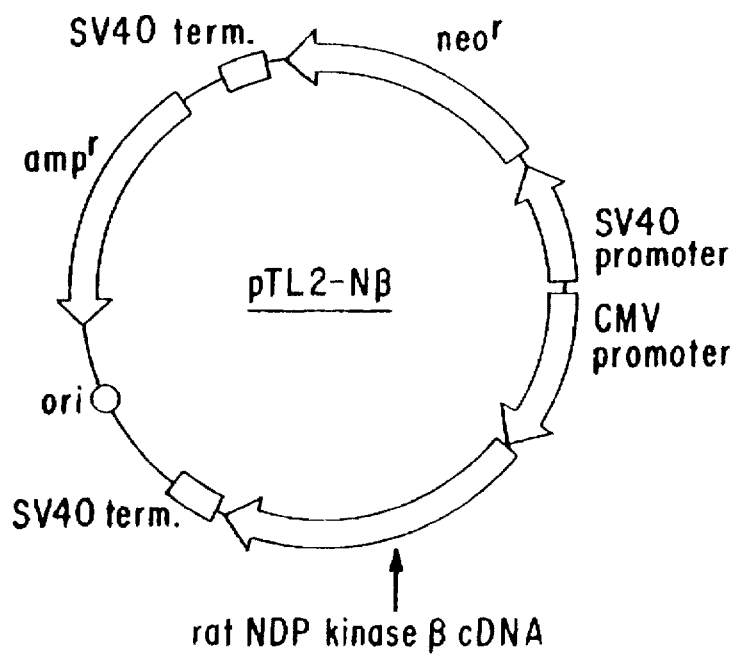
FIG. 15 illustrates the structure of the expression vector pTL2Nβ constructed in Example 9.

The two fragments were ligated, and *Escherichia coli* DH5 was transformed to screen out the desired vector pTL2Nα (FIG. 14). The desired vector was identified by partial base sequencing and preparation of the restriction map.

S.pombe was transformed in the same manner as in Example 3, and the cell extract was prepared in the same manner as in Example 4. SDS-PAGE was performed to confirm the expression of rat NDP kinase α form, and as a result, a clear band, which was not detected in the case of the control pTL2M, was detected at the position corresponding to the molecular weight of rat NDP kinase α form, about 17,000. The expression amount was measured by a densitometer and found to be from 30 to 50 wt % of the total cell protein. The protein corresponding to the band was confirmed to be rat NDP kinase α form by westernblotting using an antibody specific to rat NDP kinase α form.

EXAMPLE 9
Expression of rat NDP kinase β form

A vector including the whole cDNA of rat NDP kinase β form, pNDPKβ which was given by Dr. Narimichi Kimura at Metropolitan gerontologic research institute, was digested by restriction enzymes Nco I and Eco RI. After phenol extraction and ethanol precipitation, it was subjected to agarose gel electrophoresis. The band corresponding to a fragment of about 700 bp was cut out, and the fragment was purified by the glass beads method. Separately, pTL2M was digested by restriction enzymes Afl III and Eco RI, and after phenol extraction and ethanol precipitation, it was subjected to agarose gel electrophoresis. The band corresponding to a fragment to about 5,000 bp was cut out, and the fragment was purified by the glass beads method.

The two fragments were ligated, and *Escherichia coli* DH5 was transformed to screen out the desired vector pTL2Nβ (FIG. 5). The desired vector was identified by partial base sequencing and preparation of the restriction map.

S.pombe was transformed in the same manner as in Example 3, and the cell extract was prepared in the same manner as in Example 4. SDS-PAGE was performed to confirm the expression of rat NDP kinase β form, and as a result, a clear band, which was not detected in the case of the control pTL2M, was detected at the position corresponding to the molecular weight of rat NDP kinase β form, about 17,000. The expression amount was measured by a densitometer and found to be from 30 to 50 wt % of the total cell protein. The protein corresponding to the band was confirmed to be rat NDP kinase β form by westernblotting using an antibody specific to rat NDP kinase β form.

EXAMPLE 10
Expression of human serum albumin

PCR by Taq polymerase was conducted by using a vector pILMALB5 which includes human serum albumin cDNA and was obtained from the gene bank at the national preventive health research institute as a template, and oligodeoxyribonucleotides 5'-AGACCATGGATGCACACAAGAGTGAGGT-3'(SEQ ID NO:13) and 5'-CAGGAAACAGCTATGACCAT-3'(SEQ ID NO:14) as synthetic primers to amplify the desired fragment. After terminal modification by restriction enzymes Nco I and Hind III, phenol extraction and ethanol precipitation, it was subjected to agarose gel electrophoresis. The band corresponding to a fragment of about 1,800 bp was cut out, and the fragment was purified by the glass beads method.

Figure 16:
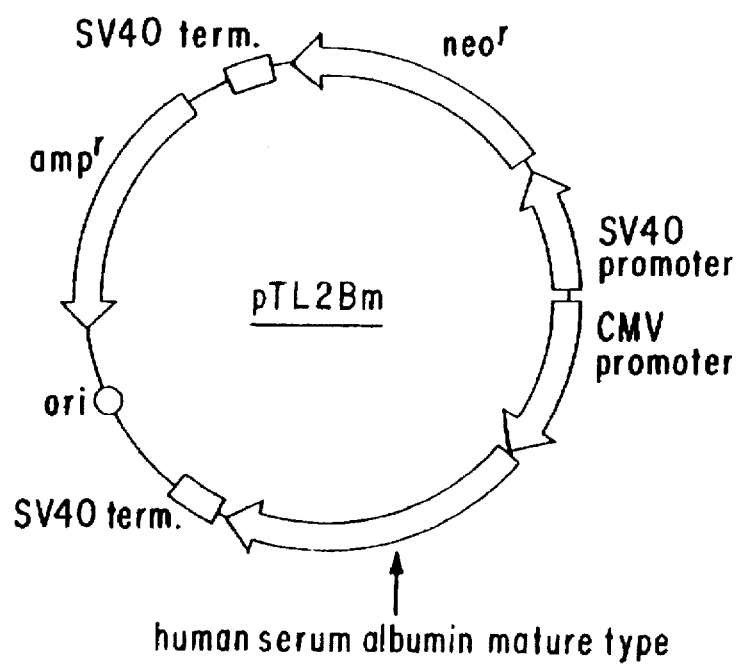
FIG. 16 illustrates the structure of the expression vector pTL2Bm constructed in Example 10.

Separately, pTL2M was digested by restriction enzymes Afl III and Hind III, and after phenol extraction and ethanol precipitation, it was subjected agarose gel electrophoresis. The band corresponding to a fragment of about 5,000 bp was cut out, and the fragment was purified by the glass beads method. The two fragments were ligated, and *Escherichia coli* DH5 was transformed by using it to screen out the desired vector pTL2Bm (FIG. 16). The desired vector has identified by partial base sequencing and preparing the restriction map.

S.pombe was transformed in the same manner as in Example 3, and the cell extract was prepared in the same manner as in Example 4. SDS-PAGE was performed to confirm the expression of human serum albumin, and as a result, a clear band, which was not detected in the case of the control pTL2M, was detected at a position corresponding to the molecular weight of human serum albumin, about 69,000. The expression amount was measured by a densitometer and found to be about 30 wt % of the total cell protein. The protein corresponding to the band was confirmed to be human serum albumin by westernblotting using an antibody specific to human serum albumin.

What is claimed is:

1. A multicloning vector for use in *Schizosaccharomyces pombe* comprising
   (a) a promoter region which functions in *Schizosaccharmyces pombe*; and
   (b) a multicloning site for introduction downstream of the promoter region of a structural gene encoding a foreign protein, wherein said structural gene is governed by a first promoter in the promoter region, and wherein a restriction enzyme recognition site in the multicloning site the vector has a sequence of 5'-ACATGT-3'.

2. The multicloning vector according to claim 1, which further comprises a second promoter and an antibiotic resistance gene governed by the second promoter, wherein the transcription decelerating activity of the second promoter is lower than that of the first promoter.

3. An expression vector for expression of a foreign protein in *Schizosaccharmyces pombe* comprising
   (a) a promoter region which functions in *Schizosaccharomyces pombe*; and
   (b) a structural gene insert at a restriction site downstream of and governed by a first promoter in the promoter region, and wherein the structural gene comprises a sequence of 5'-ACATGN-3', wherein ATG in the sequence is the translation initiation site of the structural gene, and the sequence is derived from said restriction site for introduction of the structural gene into the vector.

4. *Schizosaccharomyces pombe* transformant which carries the expression vector of claim 3, or a recombinant of the expression vector of claim 3 and a yeast vector having a replication origin.

5. A method of producing a foreign protein, which comprises
   (a) culturing the transformant of claim 4 so that the foreign protein is produced and accumulated in the culture; and
   (b) collecting the foreign protein.

6. The expression vector according to claim 3, wherein the sequence -ACATGN- is formed by ligation of -A at the 3' end of the vector and CATGN-at the 5' end of the structural gene encoding the foreign protein, or by ligation of -ACATG at the 3' end of the vector with N- at the 5' end of the structural gene encoding the foreign protein.

7. The expression vector according to claim 6, further comprising a second promoter and an antibiotic resistance gene governed by the second promoter, wherein the transcription accelerating activity of the second promoter is lower than that of the first promoter.

8. The expression vector according to claim 3, which further comprises a second promoter and an antibiotic resistance gene governed by the second promoter, wherein the transcription accelerating activity of the second promoter is lower than that of the first promoter.

9. A method of constructing an expression vector which can be expressed in *Schizosaccharomyces pombe*, comprising introducing into a vector having a promoter region which functions in *Schizosaccharomyces pombe* a structural gene encoding a foreign protein to be governed by a first promoter, wherein the structural gene is introduced downstream from the promoter region, wherein the 3' end of the vector cut at its restriction enzyme recognition site having a sequence 5'-ACATGT-3' and the 5' end of the structural gene encoding the foreign protein cut at its restriction enzyme recognition site of a sequence of -N'CATGN-, in which ATG is the translation initiation site for the structural gene encoding the foreign protein, and the combination of the 3' end of the vector cut at its restriction enzyme recognition site and the 5' end of the structural gene of the foreign protein cut at its restriction enzyme recognition site is selected so that the base next to the ATG is A, T, G, or C.

10. The method of preparing an expression vector according to claim 9, wherein the restriction site of the vector is Afl II or Nsp I, and the restriction enzyme which cuts the restriction enzyme recognition site of the structural gene encoding the foreign protein is Nco I, Bsp HI, Afl III, Nsp I or Sph I.

11. The method of constructing an expression vector according to claim 10, wherein the vector further comprises a second promoter and an antibiotic resistance gene governed by the second promoter, and the transcription accelerating activity of the second promoter is lower than that of the first promoter.

12. The method of constructing an expression vector according to claim 9, wherein the vector further comprises a second promoter region and an antibiotic resistance gene governed by a second promoter, and the transcription accelerating activity of the second promoter is lower than that of the first promoter.

* * * * *

UNITED STATES PATENT AND TRADEMARK OFFICE
CERTIFICATE OF CORRECTION

PATENT NO. : 5,817,478
DATED : October 6, 1998
INVENTOR(S) : Hideki TOHDA et al.

It is certified that error appears in the above-indentified patent and that said Letters Patent is hereby corrected as shown below:

On the title page, item [30] Foreign Application Priority Data information is incorrect. It should be:

--Oct. 5, 1993  [JP]  Japan ............5-249310--

Signed and Sealed this

Eleventh Day of May, 1999

Attest:

Q. TODD DICKINSON

Attesting Officer

Acting Commissioner of Patents and Trademarks

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
      ( A ) LENGTH: 14 base pairs
      ( B ) TYPE: nucleic acid
      ( C ) STRANDEDNESS: double
      ( D ) TOPOLOGY: linear ( i i ) MOLECULE TYPE: other nucleic acid
      ( A ) DESCRIPTION: /desc = "exemplary DNA fragment"

( x i ) SEQUENCE DESCRIPTION: SEQ ID NO:1:

NNNNACATGG NNNN                                                                                      14

( 2 ) INFORMATION FOR SEQ ID NO:2:

( i ) SEQUENCE CHARACTERISTICS:
      ( A ) LENGTH: 14 base pairs
      ( B ) TYPE: nucleic acid
      ( C ) STRANDEDNESS: double
      ( D ) TOPOLOGY: linear ( i i ) MOLECULE TYPE: other nucleic acid
      ( A ) DESCRIPTION: /desc = "exemplary DNA fragment"

( x i ) SEQUENCE DESCRIPTION: SEQ ID NO:2:

NNNNACATGA NNNN                                                                                      14

( 2 ) INFORMATION FOR SEQ ID NO:3:

( i ) SEQUENCE CHARACTERISTICS:
      ( A ) LENGTH: 14 base pairs
      ( B ) TYPE: nucleic acid
      ( C ) STRANDEDNESS: double
      ( D ) TOPOLOGY: linear ( i i ) MOLECULE TYPE: other nucleic acid
      ( A ) DESCRIPTION: /desc = "exemplary DNA fragment"

( x i ) SEQUENCE DESCRIPTION: SEQ ID NO:3:

NNNNACATGT NNNN                                                                                      14

( 2 ) INFORMATION FOR SEQ ID NO:4:

( i ) SEQUENCE CHARACTERISTICS:
      ( A ) LENGTH: 14 base pairs
      ( B ) TYPE: nucleic acid
      ( C ) STRANDEDNESS: double
      ( D ) TOPOLOGY: linear ( i i ) MOLECULE TYPE: other nucleic acid
      ( A ) DESCRIPTION: /desc = "exemplary DNA fragment"

( x i ) SEQUENCE DESCRIPTION: SEQ ID NO:4:

NNNNACATGC NNNN                                                                                      14

( 2 ) INFORMATION FOR SEQ ID NO:5:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: other nucleic acid ( x i ) SEQUENCE DESCRIPTION: SEQ ID NO:5:

TTGACTAGTT ATTAATAGTA                                                      20

( 2 ) INFORMATION FOR SEQ ID NO:6:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:6:

CTAGAATTCA CATGTTTGAA AAAGTGTCTT TATC                                      34

( 2 ) INFORMATION FOR SEQ ID NO:7:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:7:

ATGCCATGGC AATGGTATCA GAATT                                                25

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:8:

AGCCAGTATA CACTCCGCTA                                                      20

( 2 ) INFORMATION FOR SEQ ID NO:9:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:9:

GACTCATGAG CTCCAAGCCA AAGCC                                                25

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:10:

TTCCCAGTCA CGACGTTGTA                                                      20

( 2 ) INFORMATION FOR SEQ ID NO:11:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:11:

ATCGCATGCC AGTACCCCCA GGAGAAGA                28

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:12:

TGAAAATCTT CTCTCATCCG                20

( 2 ) INFORMATION FOR SEQ ID NO:13:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:13:

AGACCATGGA TGCACACAAG AGTGAGGT                28

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:14:

CAGGAAACAG CTATGACCAT                20

( 2 ) INFORMATION FOR SEQ ID NO:15:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

Met Val Ser Glu
1